United States Patent [19]
Martinelli et al.

[11] Patent Number: 5,407,798
[45] Date of Patent: Apr. 18, 1995

[54] AMPLIFICATION OF MIDIVARIANT DNA TEMPLATES

[75] Inventors: Richard A. Martinelli, Brighton; Jeffrey J. Donahue, Wayland; John T. Unger, Medfield, all of Mass.

[73] Assignee: Ciba Corning Diagnostics Corp., Medfield, Mass.

[21] Appl. No.: 15,249

[22] Filed: Feb. 5, 1993

Related U.S. Application Data

[63] Continuation of Ser. No. 598,269, Oct. 16, 1990, abandoned.

[51] Int. Cl.$^6$ .......................... C12Q 1/68; C12P 19/34
[52] U.S. Cl. ...................................... 435/6; 435/91.1; 935/77; 935/78
[58] Field of Search ................... 435/6, 91, 91.1; 935/77, 78

[56] References Cited

U.S. PATENT DOCUMENTS

| | | | |
|---|---|---|---|
| 4,786,600 | 11/1988 | Kramer et al. | 435/235 |
| 4,883,750 | 11/1989 | Whiteley et al. | 435/6 |
| 5,112,734 | 5/1992 | Kramer et al. | 435/6 |

FOREIGN PATENT DOCUMENTS

| | | |
|---|---|---|
| 9006376 | 6/1990 | WIPO . |
| 9014439 | 11/1990 | WIPO . |

OTHER PUBLICATIONS

Lizardi et al., Bio/Technology 6(10):1197-1202 (Oct. 1988).
WO-A-9002820 entitled "Replicative RNA-based amplification/detection systems".
EP-A-0361983 entitled "Nucleic acid amplification using a single primer".
WO-A-9003446 entitled "Nucleic acid probes containing improved molecular switch, and assays and kits incorporating same".
EP-A-0379369 entitled "RNA template end-linked probe constructs and methods of use".
Feix et al., FEBS Lett. 63(1):201-204 (Mar. 1976).
Zhang, Diss. Abstr. Intl. 53/11-B:5568 (1992) (Ph.D. thesis/abstr.).
Cahill, et al., Clin. Chem. 37(9), 1482-1485 (1991), "Polymerase Chain Reaction and QB Replicase Amplification".
Kramer, et al., Nature, 339, 401-402 (Jun. 1, 1989), "Replicable RNA Reporters".
Kramer et al., Trends in Biotechnology 9, 53-58 (Feb. 1991), "Exponential Amplification of Nucleic Acids: New Diagnostics Using DNA. Polymerases and RNA Replicases".

Primary Examiner—Stephanie W. Zitomer
Attorney, Agent, or Firm—Nicholas I. Slepchuk, Jr.; Arthur S. Morgenstern; Judith A. Roesler

[57] ABSTRACT

New methods are provided for the amplification of a midivariant DNA containing an inserted target specific nucleic acid sequence(s) to enable detection of the presence of a target nucleic acid sequence in a test sample. One method employs midivariant DNA as a template for the synthesis of RNA catalyzed by QB replicase. Two midivariant DNA/probe conjugates including a nonreplicable portion of midivariant DNA and a target specific nucleic acid sequence (probe) are described. An amplification method including the steps of hybridization and ligation of the midivariant DNA/probe conjugates followed by replication of the DNA template has enabled detection of less than 200 template molecules. In a modified amplification method one of the midivariant DNA/probe conjugates further includes a RNA polymerase promoter sequence to enable transcription of the midivariant DNA template into RNA. The sequential ligation-transcription-replication method enables the detection of a single template molecule. The detectable molecule(s) are indicative of the presence of the target nucleic acid sequences in the test sample.

16 Claims, 9 Drawing Sheets

AMPLIFICATION OF MIDIVARIANT DNA TEMPLATES

This is a continuation of application Ser. No. 07/598,269, filed on Oct. 16, 1990, and now abandoned.

BACKGROUND OF THE INVENTION

1. Field of the Invention

The present invention generally relates to amplification methods and more particularly, amplification including midivariant DNA/probe conjugates.

2. Technical Review

Nucleic acid based test assays provide distinct advantages in specificity and sensitivity over conventional immunoassay procedures. The essential feature of nucleic acid based test assays is the hybridization of target specific nucleic acid sequences (probes) to their complementary target nucleic acid sequences in a test sample. A probe's specificity relates to its ability to distinguish between target and non-target nucleic acid sequences. Probe specificity may be absolute (i.e. probe able to distinguish between target nucleic acid sequences and non-target nucleic acid sequences), or it may be functional (i.e. probe able to distinguish between the target nucleic acid sequence and any other nucleic acid sequence normally present in a test sample). A target nucleic acid sequence of a test sample in a test assay refers to a segment of single-stranded polynucleotide having a nucleotide base sequence corresponding to a genetic element whose presence in a test sample is to be determined. The test sample refers to any test sample containing one or more target nucleic acids and which may be in purified or nonpurified form. Sources for test sample may include, but should not be limited to, physiological and nonphysiological DNA or RNA (synthesized or natural), and the like.

It has been noted that the whole repertoire of antigenic determinants of two separate but related organisms may not permit their discrimination by immunoassay, whereas unique genomic sequences can be identified and differentiated by a nucleic acid test assay. See U.S. Pat. No. 4,851,336. Also, in the case of viral targets, i.e. HIV infection, antibodies to viral antigens may not be detectable even though viral sequences have been inserted into the host genome, however, the insertion will provide a potential diagnostic marker if a detection (amplification) methodology of the requisite sensitivity can be devised. The present invention provides amplification methodology(s) of the requisite sensitivity.

It is now realized that the full capability, in terms of sensitivity, of nucleic acid based test assays can only be achieved in conjunction with a method for the amplification of a detectable molecule indicative of the presence of the target nucleic acid sequence in the test sample.

The polymerase chain reaction (PCR) is one type of amplification method where the target sequence is first amplified and then isolated. Since PCR amplification occurs early in the process, sequences other than the target may also amplify. Identification of the actual target requires the analysis of the amplified sequences. See U.S. Pat. Nos. 4,683,195 and 4,683,202.

U.S. Pat. Nos. 4,786,600 and 4,957,858 describe an autocatalytic replication of recombinant RNA by QB replicase, another type of amplification method where the target sequence is first isolated and then amplified. The disadvantage of this method of QB amplification is that probes not hybridized to the target nucleic acid sequence must be made vulnerable to destruction i.e. rendered unreplicable. See "Amplifying Probe Assays with Q-Beta Replicase" *Bio/Technology* 1989: 7(6), 609–10 (Eng.) and "Q Beta Amplification" *J. Clin. Lab. Anal.* 4:318 (1990) (letter).

SUMMARY OF THE INVENTION

An amplification method(s) is described and includes as a first step the hybridization of two distinct nonreplicable midivariant DNA/probe conjugates to a target nucleic acid sequence in a test sample. The test sample being previously treated, if necessary, to release the target nucleic acid sequences. These conjugates each include at least two parts, one part consists of a target specific nucleic acid sequence (probe), which is complementary to that of the target nucleic acid sequence, under hybridization conditions, and the other part being a nonreplicable portion of the midivariant DNA. One conjugate will contain a portion of the 5' end of one strand of the midivariant DNA and the other conjugate will contain the remaining nonreplicable portion of the midivariant DNA to its 3' terminus. The probes of the conjugates are chosen so that upon hybridization to the target molecule the two probes are aligned contiguous to each other. In the next step the probes are covalently coupled by T4 DNA ligase to generate a substrate for replication. The enzyme QB replicase uses the midivariant DNA as a template to produce copies of the RNA midivariant sequence with the target specific sequence inserted. The products of the replication are detected and are indicative of the presence of target molecule in the test sample.

In a modified amplification method one of the portions of the nonreplicable midivariant DNA of one conjugate includes an attached RNA polymerase promoter. The RNA polymerase promoter operates as a double stranded molecule. Following hybridization and ligation the DNA template is transcribed into RNA. The RNA transcript is then replicated by QB replicase, and the replication product detected.

A conjugate and a pair of conjugates are described for use in the amplification method(s) of the present invention.

The midivariant DNA/probe conjugates and other components as described herein are adapted to be packaged in a test kit for performing the amplification method(s).

It is a primary objective of the invention to provide an amplification method incorporating midivariant DNA.

It is still another object of the invention to provide a conjugate including a nonreplicable portion of midivariant DNA and a target specific nucleic acid sequence.

A further objective of the invention is to provide two distinct conjugates, each including, a distinct nonreplicable portion of midivariant DNA and a distinct target specific nucleic acid sequence, and where upon hybridization of both target specific nucleic acid sequences to a target nucleic acid sequence in a test sample, the probes are ligated and the portions of the midivariant DNA then serve as a template for replication, with the products of the replication being detectable.

Another object of the invention is to provide an amplification method, including hybridization, ligation and replication steps that permit the detection of less than 200 target molecules in a test sample.

A still further object of the invention is to provide a modified amplification method including hybridization, ligation, transcription and replication steps that permit the detection of one target molecule in a test sample.

It is still another objective of the invention to provide a test kit for performing an amplification method in order to detect replication products indicative of the presence of a target nucleic acid sequence in a test sample.

Another objective of the invention is to provide an amplification method which affords significant advantage of sensitivity compared to immunoassays.

BRIEF DESCRIPTION OF THE DRAWINGS

The foregoing and other objects and advantages of the invention will be appreciated more fully from the following further description thereof with reference to the accompanying drawings wherein.

DESCRIPTION OF THE PREFERRED EMBODIMENT

In the examples provided below the product of the replication step of the amplification methods is detected by radioisotopic techniques. In a preferred embodiment, however, the products of the replication step of the amplification are detected by chemiluminescent methodology. See U.S. Pat. No. 4,745,181. An immunoassay format representative of this methodology in the case of probe technology, provides that a complementary "reagent" sequence directed toward a target molecule of interest believed to be present in a test sample is immobilized upon paramagnetic particle (PMP) (Ciba Corning Diagnostics Corp.), a solid phase, and a second complementary "reagent" sequence to the target molecule is labelled with an acridinium ester (Ciba Corning Diagnostics Corp.). Upon incubation of the reagents with the test sample, a sandwich complex is formed with the target molecule. A magnetic field is applied and the PMP are separated out of solution, this effects a separation of the unbound acridinium ester labelled complementary reagent sequence from that which is specifically bound to the analyte on the PMP. After this separation step, the target sequence is detected by the chemiluminescent reaction of labelled complementary reagent sequence which has remained bound to the PMP. In the present invention this chemiluminescent methodology may be applied to detect the replication products. The amplification methodology may also be applied to immunoassays.

Nucleic acid sequences unique to and indicative for certain pathogens in various test samples have been reported. The source of target nucleic acid sequences in a test sample is defined to include, but not be limited to, cells, viruses and viroids. Although some test samples have been shown by quantitative culture methods to contain as high as $10^7$–$10^9$ cells of the infectious organism, in some Salmonella test samples as few as 1000 organisms per gram were shown present.

The current limit of sensitivity of chemiluminescent based detection methodology is approximately 100 amol (60 million molecules). This level of sensitivity was observed for an assay in which a chemiluminescent labelled DNA oligomer was hybridized to Campylobacter 16S ribosomal RNA. Since the required sensitivity of these assays, for example, for infectious disease agents must be as low as 1000 molecules, the target molecules must be amplified by at least $10^4$–$10^5$ in order to be detected by chemiluminescent based detection methodology.

A means of obtaining the necessary sensitivity for these test assays involves an amplification method incorporating the use of the enzyme QB replicase. See "Autocatalytic Replication of a Recombinant RNA" *J. Mol. Bio.* 171:281–95 (1983) and U.S. Pat. No. 4,786,600 which is incorporated herein by reference. The QB virus is an RNA phage whose genome consists of a strand of approximately 4400 ribonucleotides. See Blumenthal, (1982) In "The Enzyme" (Vol. XV, Part B) (P. D. Boyer, ed.) p. 267, Academic Press, New York. The role of QB replicase is to catalyze the synthesis of the complementary strand of RNA from this RNA template. The enzyme consists of 4 subunits, only one of which is actually coded for by the viral genome, the other subunits are derived from the bacterial host. Although QB replicase exhibits narrow specificity in that it will only use QB RNA as a template for complementary strand synthesis for replication (other viral RNA sequences are not replicated), shorter, naturally occurring mutants of QB RNA can also serve as templates for replication. These shorter templates include "nanovariant" RNA which is 90 ribonucleotides in length and "midivariant" RNA which is 220 nucleotides in length.

Figure 1:
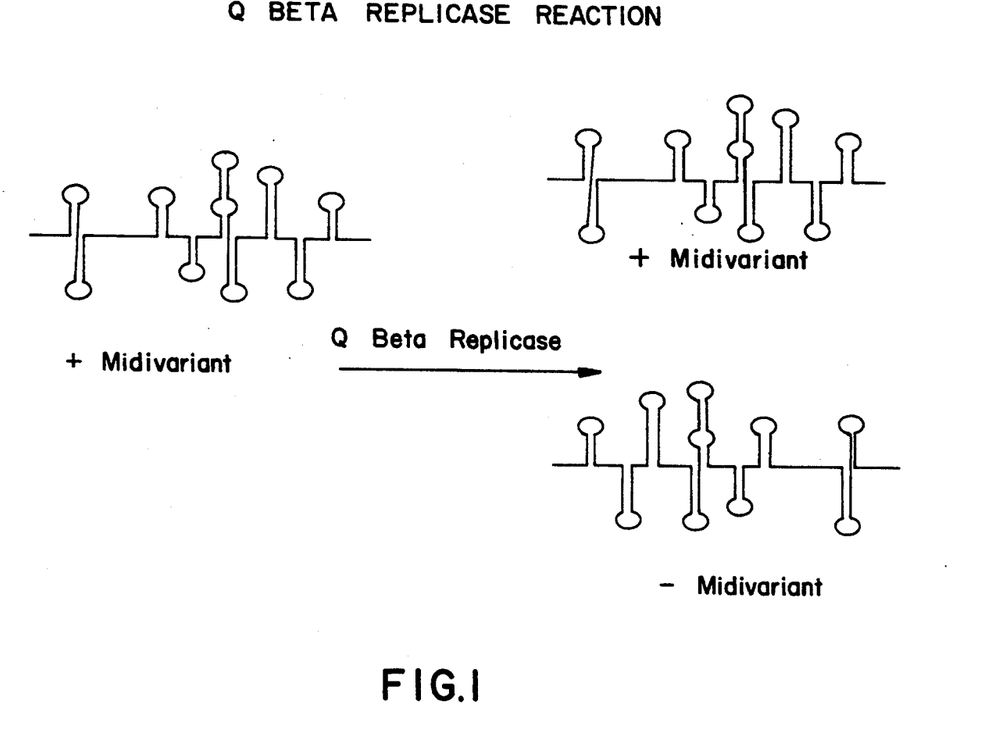
FIG. 1 is a representative illustration of replication catalyzed by QB replicase.

Referring to FIG. 1, the action of QB replicase is illustrated as follows: starting with a single copy of midivariant (MDV) RNA, which is symbolized by the stem and loop model of its predicted secondary structure, the strand is used as a template for the synthesis of the complementary minus strand. After N rounds of replication, there will be $2^N$ strands produced for each initial template strand. As long as the enzyme is in molar excess over the RNA strands produced, there will be an exponential production of product RNA.

In the preferred amplification method of the present invention the midivariant (+) DNA template is divided into two nonreplicable portions for example, at base 61 from the 5' end of the plus strand SEQ. NO.:1 and SEQ. NO.:2. To each of the two portions of the midivariant DNA is added a distinct target specific nucleic acid sequence which is complementary to a target nucleic acid sequence to form a conjugate. The analogous complementary sequences of the midivariant (−) DNA may be utilized in a similar manner SEQ. NO.:3 and SEQ. NO.:4. The two conjugates are designated Probe A and Probe B, respectively, see FIG. 2. Probe A has been immobilized upon PMP. One conjugate includes a nonspecific base sequence at its 5-prime terminus which includes at least two nucleotides and wherein at least one nucleotide includes a reactive group comprising a primary amine. The immobilization of a conjugate on a solid support, however, is not a requirement nor limitation of the present invention. The test sample is lysed to release the target nucleic acid sequences. The released target nucleic acid sequences are hybridized with Probe A and Probe B under hybridizing conditions. The target specific sequences are chosen so that upon hybridization to the target, the two target specific sequences are aligned contiguous to each other. After hybridization, the PMP are separated from the test sample components and unhybridized Probe B and non-targeted nucleic acid sequences.

Figure 2:
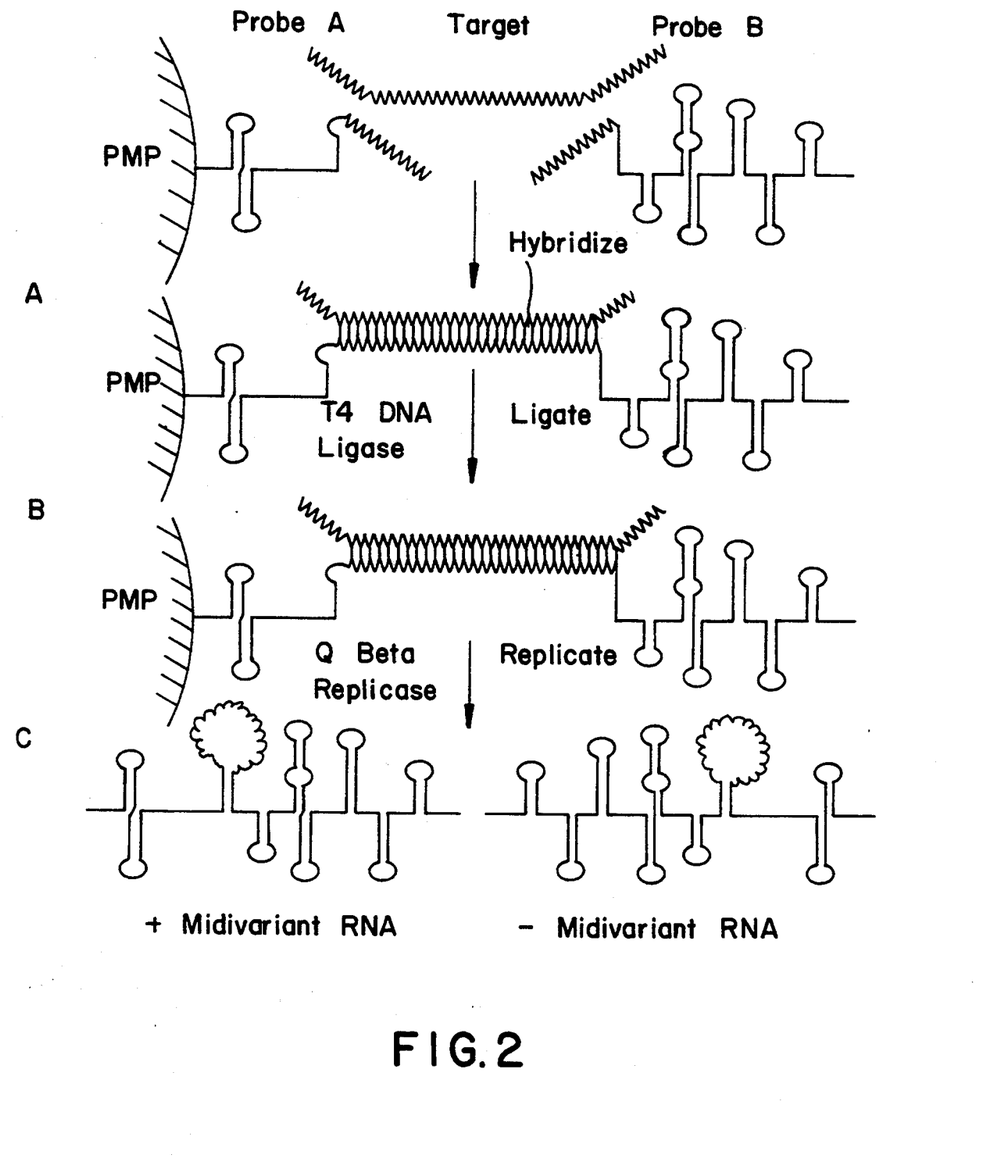
FIG. 2 is a representative illustration of the hybridization-ligation-replication method of the present invention.

Probes A and B which have been hybridized to the target sequence are then joined covalently by the action of DNA ligase which catalyzes the formation of a phosphodiester bond between the two Probes, see FIG. 2B. The conjugates may be released from the solid phase before or after the ligation step. Following this ligation step a midivariant (+) DNA template has been generated in a manner that depends upon the presence of the target molecule in the test sample. Inserted into this midivariant (+) DNA sequence is the combined target specific sequences from Probe A and Probe B. The midivariant template with the inserted target specific sequences can now be replicated with QB replicase. The products of the replication are detectable and thereby indicative of the presence of the target in the test sample.

For this ligation-replication method to work it is desirable that neither Probe A or Probe B alone can serve as a replicable template. In addition, the insertion of target specific sequences into the midivariant template at the position chosen must not unduly perturb those features required for its recognition by QB replicase, see FIG. 2C.

Figure 3:
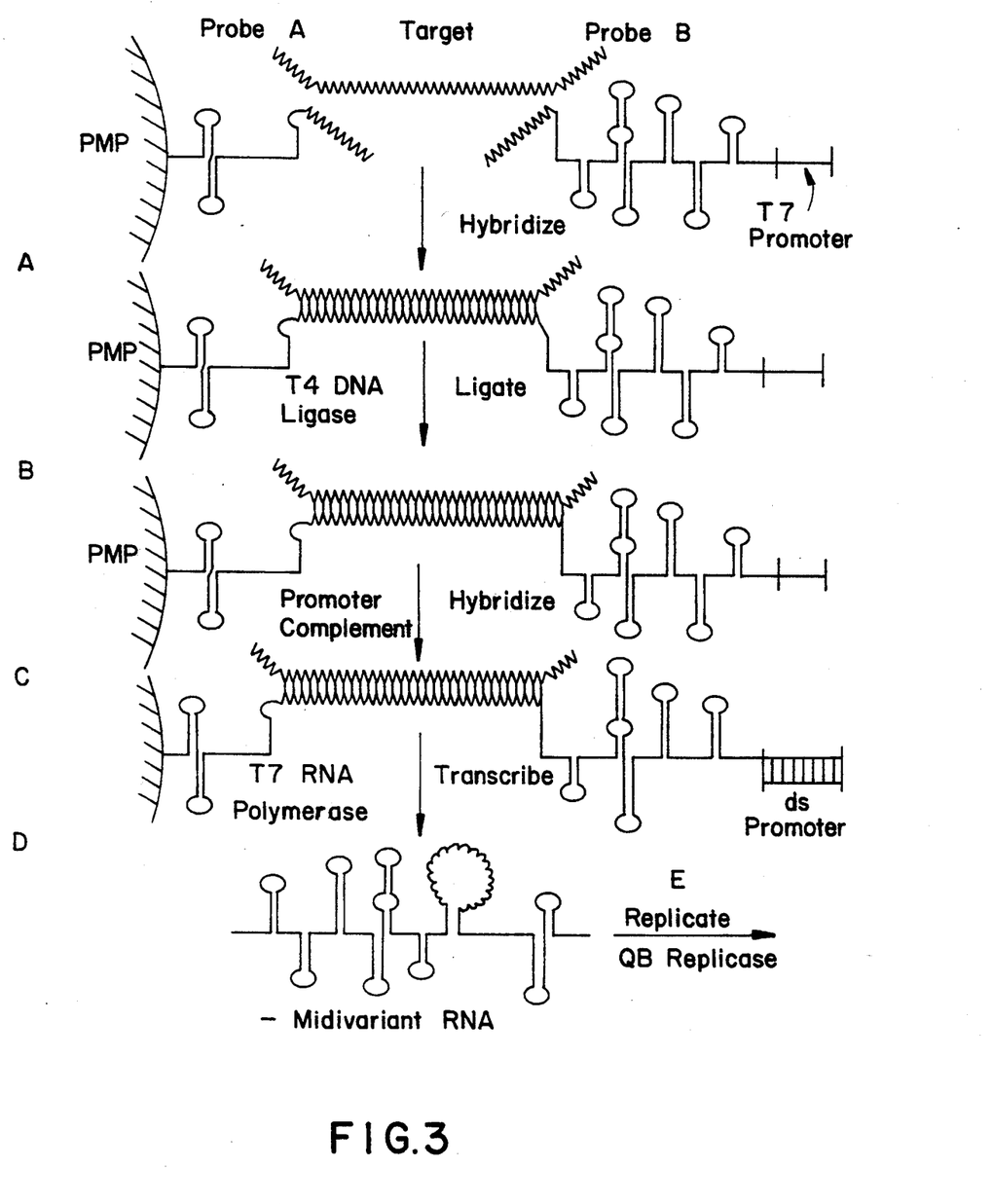
FIG. 3 is a representative illustration of the hybridization-ligation-transcription-replication method of the present invention.

In a modification of this amplification method the ligated midivariant DNA is transcribed into RNA before the replication by QB replicase. A polymerase promoter is attached to a nonreplicable portion of midivariant DNA before the transcription step. The ligation-transcription-replication method enables the detection of a single template. See FIG. 3.

Figure 4:
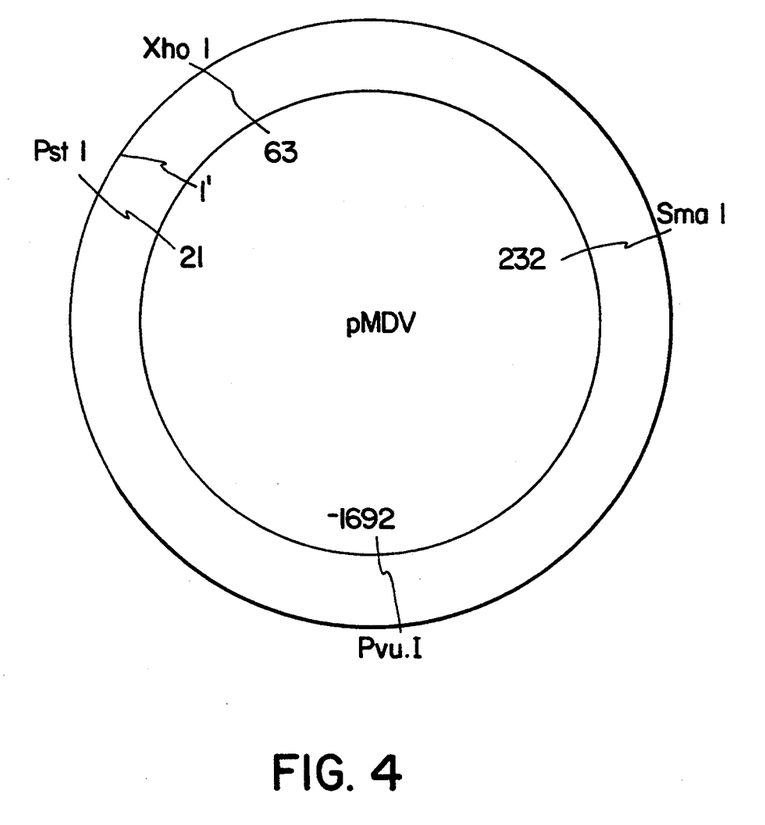
FIG. 4 is a partial restriction map of pMDV.

A plasmid containing the midivariant sequence (pMDV) (Promega, Madison, Wis.) was used to transform bacterial cells (JM107), the transformed cells grown in culture, the cultured cells harvested and lysed, and the plasmid purified, all by standard procedures. See Example 1. Samples of pMDV were digested with the restriction enzymes Pst I, Sma I, Xho I, or combinations of these enzymes to obtain the fragments of pMDV as indicated in the restriction map shown in FIG. 4. The pMDV contained a 10 base pair Xho I linker at position 61 of the plus strand.

Other versions of the midivariant sequence were prepared and tested for their capability to serve as replication templates. Advantage was taken of the Xho 1 restriction site in order to insert foreign target specific sequences. Insertions made into the natural midivariant sequence may be used to hybridize with desired target sequences and facilitate the use of midivariant DNA in amplification methods so long as the inserted target specific sequences permit the recombinant molecules to act as templates for RNA synthesis. Table I lists examples of inserted sequences at the Xho I restriction site.

All versions of midivariant DNA were base treated to remove possible RNA contaminants prior to inclusion in replication reactions. Intact plasmid and restriction enzyme digested plasmids were incubated at 80° C. in 1N NaOH for 15 min. and then neutralized by addition of an equivalent of HCl prior to incorporation in replicase reactions in order to remove contaminating RNA templates. A sample of each of the putative DNA template was also digested with DNase (Promega) and the digested templates also tested for residual capability to serve as a substrate for QB replicase.

Midivariant DNA samples were then tested for their ability to serve as templates for RNA synthesis with QB replicase. The replicase reactions contained 100 mM Tris-HCl, pH 7.5, 15 mM $MgCl_2$, 1 mM each ATP, GTP, UTP, and CTP. Alpha $^{32}$P-CTP (New England Nuclear) was utilized as a label to detect synthesized RNA products. The QB replicase concentration was 20 ug/ml and reactions incubated for 1 hr. at 37° C. The replication reaction was assayed by spotting an aliquot of the reaction on a GFF filter (Whatman), precipitating the synthesized RNA by immersing the filter in ice cold 10% trichloroacetic acid/1% sodium pyrophosphate. The filters were washed four times with ice cold 5% trichloroacetic acid and then counted by liquid scintillation. The results of these replication experiments are summarized in Table II and establish the ability of the intact midivariant DNA sequence, whether in linear or closed circular form, to act as a template for QB replicase directed RNA synthesis. It was further observed that the RNA product synthesized from midivariant DNA templates hybridized with pMDV but not to a plasmid containing the nanovariant DNA sequence (data not shown).

In order to test the sensitivity of replication of midivariant templates with inserted sequences, the sequences were cloned into an Xho site of a plasmid containing the midivariant sequence as described above. The sensitivity of replication reactions of these midivariant DNA templates are summarized in Table III. These data were obtained by measuring the incorporation of $^{32}$P-CTP into the RNA replication product. These data indicate that the end product of the ligation-replication scheme, see FIG. 2, is a template for QB replicase and that as few as 160 template molecules (MDV-SA2) could be detected. The replication products were further characterized by Northern blotting and the inserted target specific sequences were found to be replicated along with the flanking midivariant sequences (data not shown).

It was noted that some of the QB replicase enzyme preparations utilized contained a DNase contamination. This contamination may interfere with replication sensitivity by degrading the DNA templates. The removal of the DNase contaminant by alternative purification schemes or the use DNase inhibitors may be required where contamination is present. An alternative approach to obtain better replication sensitivity is to obtain an enzyme which replicates DNA templates more efficiently than QB replicase. QB replicase itself might be modified by site-directed mutagenesis to produce a more efficient enzyme.

Figure 5:
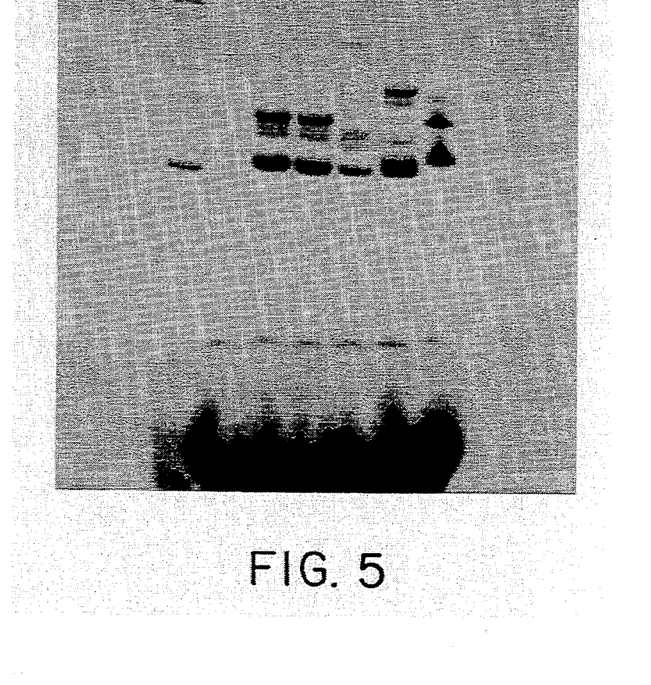
FIG. 5 illustrates the results of gel electrophoresis of products of the replication of the present invention.
Figure 6:
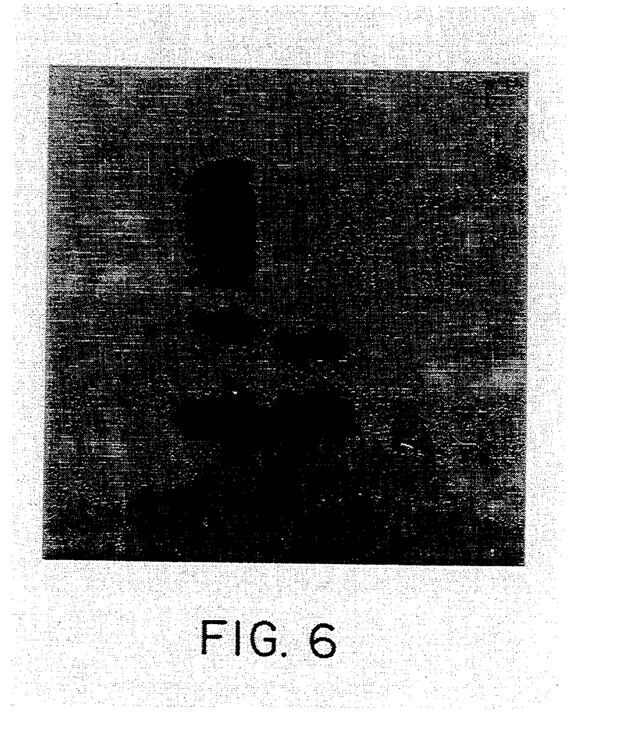
FIG. 6 illustrates the results of gel electrophoresis for the hybridization-ligation-replication reaction of Example 3.
Figure 7:
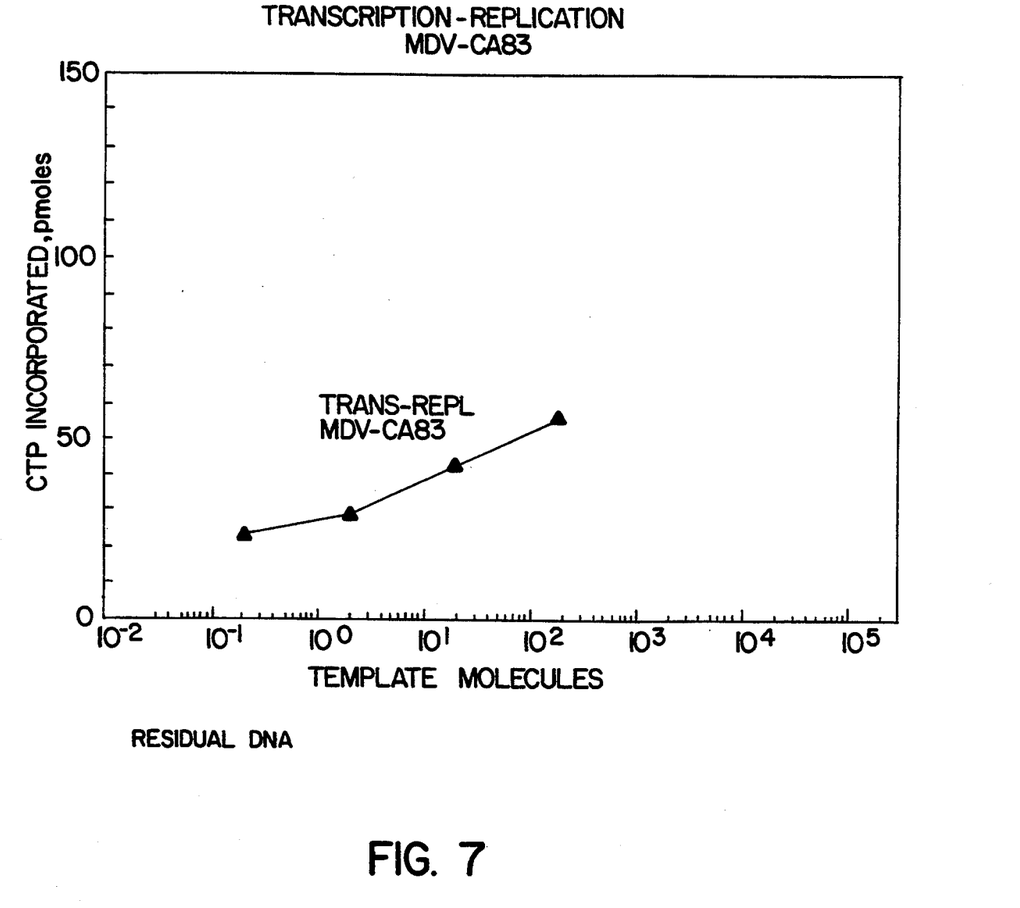
FIG. 7 illustrates the results of the transcription-replication reaction with MDV-CA83 of Example 4.
Figure 8:
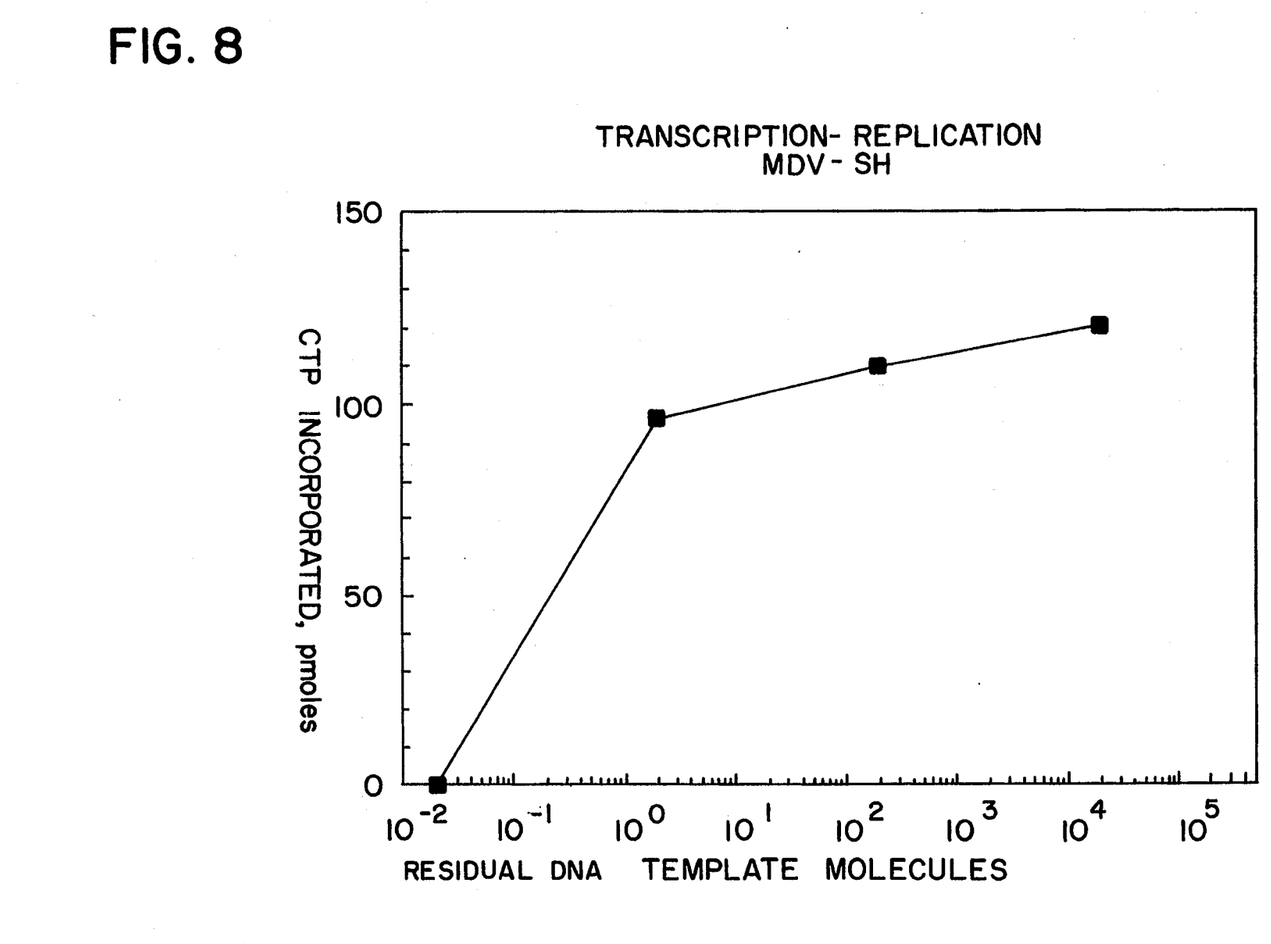
FIG. 8 illustrates the results of the transcription-replication reaction with MDV-SH of Example 4.
Figure 9:
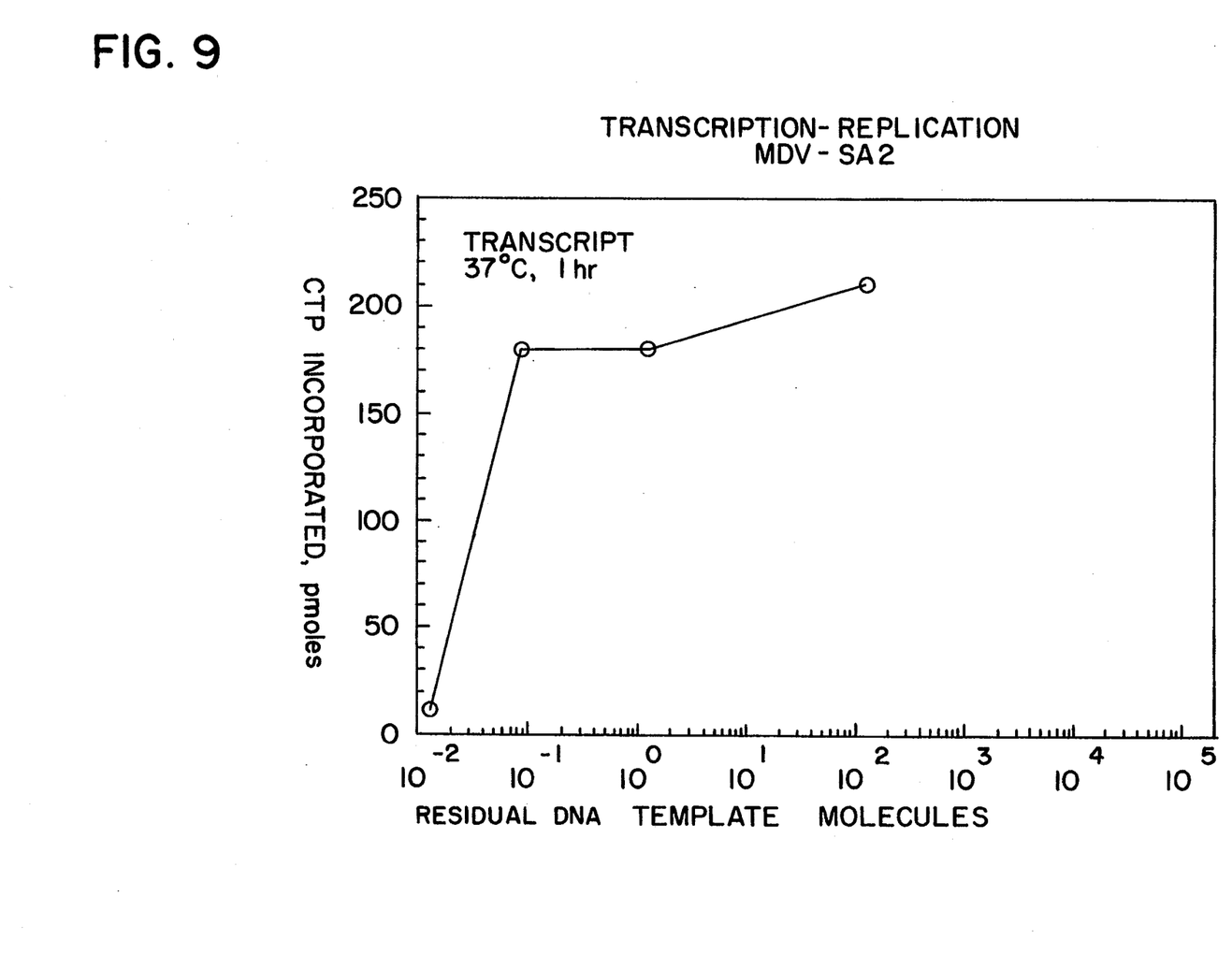
FIG. 9 illustrates the results of the transcription-replication reaction with MDV-SA2 of Example 4.

The products of the reaction of QB replicase and the various midivariant DNA templates were further characterized by denaturing polyacrylamide gel electrophoresis. Gel electrophoresis results of some of the $^{32}$P labelled midivariant replication products are shown in FIG. 5. Midivariant DNA templates were incubated with QB replicase at 30° C. for 2 hrs. Samples from each reaction were incubated in loading buffer containing 7M urea at 70° C. for 5 min. prior to electrophoresis. The samples were electrophoresed on a 6% polyacrylamide gel that contained 7M urea in a Tris borate EDTA buffer. After electrophoresis the bands were visualized by autoradiography. Referring to FIG. 5 the samples applied to the lanes (left to right) are as follows: lane 1: 123 bp ladder (BRL) as a size marker; lane 2: zero template control; lane 3: replication products from pMDV template; lane 4: replication products from MDV template; lane 5: replication products from MDV-CA 116 template; lane 6: replication products from MDV-CA 29 template; and lane 7: replication products from MDV-poly template. In addition to the expected size full length replication products, for each template many additional products were observed which migrated faster than the full length products. The faster migrating bands have been shown to hybridize with probes complementary to portions of the midivariant plus strand and the minus strand (data not shown).

The replication products from the midivariant templates were further characterized by Northern blotting to determine whether the inserted sequences were replicated along with the flanking midivariant sequences. These blots were probed with a Campylobacter specific probe, PM238 (Promega) for the templates containing inserts of Campylobacter sequences or a polylinker specific probe, PM905 (Promega), see Table I. The replication products from MDV-CA 29 and MDV-CA 116 hybridized with PM238 while the replication products from MDV-poly hybridized with PM905 (data not shown). The results demonstrate that the inserted sequences replicate along with flanking midivariant sequences.

EXAMPLE 1

Replication Sensitivity of Midivariant DNA Templates

A plasmid containing a midivariant (pMDV) sequence and having a 10 base pair insertion to generate an Xho I linker was obtained from Promega, Inc., Madison, Wis. The rest mentary in sequence to portions of MB2 and MB1SA1. This hybridization aligns the midivariant sequence at the 3' terminus of MB1SA1 adjacent to the midivariant sequence at the 5' terminus of MB2. These two oligomers were ligated together by T4 DNA ligase (Promega). The ligated product, MBSA1, was purified from the reaction mixture by preparative 6% denaturing polyacrylamide gel electrophoresis. As a zero target control, the PMP and MBSA1 were incubated alone in the absence of PM2058 under the same conditions. The PMP were separated and the supernatant removed. The PMP were washed twice with 2X SSC/0.1% Tween-20.

The PMP were resuspended in 100 ul of ligase buffer (BRL) containing 20 U T4 DNA ligase (BRL) and incubated at room temperature for 1 hr. As a control to determine the necessity of ligation, an equivalent sample of hybridized PMP were incubated in the ligase buffer without T4 DNA ligase. The PMP were separated and the supernatant removed; the PMP were then washed twice with 2X SSC/0.1% Tween-20 and resuspended in 100 ul water.

One ul aliquots from each ligation sample was incubated with 20 ug/ml QB replicase (Lot M202) (Promega) in 100 mM Tris-HCl, pH 7.5, 15 mM $MgCl_2$, and 1 mM each ATP, GTP, UTP, and CTP. Alpha $^{32}$P-CTP (Amersham) 800 Ci/mmol was included to give a specific activity of approximately $10^5$ cpm/nmol CTP. CTP incorporation was determined as described in Example 1. The replication reactions were also analyzed by denaturing 6% polyacrylamide gel electrophoresis.

The results for CTP incorporation are summarized in Table V and the results of the gel electrophoresis are shown in FIG. 6. Referring to FIG. 6 the samples applied to the lanes (left to right) are as follows: lane 1:123 bp ladder (BRL) as a size marker; lane 2: ligated template replication product; lane 3: Minus PM2058 Control, replication product; and lane 4: Minus ligase control, replication product. The absence of replication in the negative control sample confirms the results from Example 2 that the probes do not replicate under the conditions of the test assay.

EXAMPLE 4

Sensitivity of Sequential Transcription-Replication

The Pst I/Sma I fragments of the midivariant plasmids containing target specific inserts including, for example, Salmonella, Shigella, and Campylobacter were prepared and gel purified. These Pst I/Sma I fragments contain a T7 promoter that enables a transcript of the plus strand of the midivariant template be be produced by the action of T7 RNA polymerase. Dilutions of the Pst I/Sma I fragments were incubated with T7 RNA polymerase (Promega) 3 U/ul for 1 hr. at 37° C. in 40 mM Tris-HCl, pH 8.0, also 10 mM NaCl, 6 mM $MgCl_2$, 2 mM spermidine, 10 mM dithiothreitol, and 3 mM each of ATP, CTP, GTP and UTP, in a total volume of 25 ul. A 2 ul aliquot of the transcription reaction product was then incubated with QB replicase under the standard replication reaction conditions described in the preceding Examples except that the incubation was for 1 hr. at 37° C. CTP incorporation was measured as described in Example 1. The results of the transcription-replication reactions are shown in FIGS. 7, 8 and 9 for MDV-CA83, MDV-SH, and MDV-SA2, respectively. These data indicate that transcription occurred even for the lowest amount of template present and between 10 and 100 RNA copies are produced per DNA template. The RNA transcripts were efficiently replicated by QB replicase. The combined transcription-replication allowed for the detection of templates at the single molecule level.

It is to be understood that various other modifications will be apparent to and can readily be made by those skilled in the art, given the disclosure herein, without departing from the scope and materials of this invention. It is not, however, intended that the scope of the claims appended hereto be limited to the description as set forth herein, but rather that the claims be construed as encompassing all features of patentable novelty which reside in the present invention, including all features which would be treated as equivalents thereof by those skilled in the art to which the invention pertains. It is also noted that the examples given herein are intended to illustrate, and not to limit the invention.

TABLE I

| | | |
|---|---|---|
| Poly: | 26 bp | polylinker sequence (Promega) |
| SA1: | 48 bp | Salmonella sequence (Promega) |
| SA2: | 48 bp | Salmonella sequence (Promega) |
| SH: | 60 bp | Shigella sequence (Promega) |
| CA: | 60 bp | Campylobacter sequence (Promega) |
| CA29: | 29 bp | Campylobacter 16S rRNA sequence |
| CA83: | 83 bp | Campylobacter 16S rRNA sequence |
| CA116: | 116 bp | Campylobacter 16S rRNA sequence |

TABLE II

REPLICATION OF MIDIVARIANT PLASMID FRAGMENTS

| TEMPLATE | TREATMENT | CTP INCORPORATED (pmol) |
|---|---|---|
| pMDV | Base | 720 |
| pMDV | Base/DNase | 14 |
| pMDV/Pst I | Base | 420 |
| pMDV/Pst I | Base/DNase | 10 |
| pMDV/Sma I | Base | 460 |
| pMDV/Sma I | Base/DNase | 7 |
| MDV | Base | 590 |
| MDV | Base/DNase | 22 |
| pMDV/Xho 1/Pvu I Larger Fragment | Base | 0 |
| pMDV/Xho I/Pvu I Smaller Fragment | Base | 28 |

TABLE III

REPLICATION SENSITIVITY OF DNA TEMPLATES

| TEMPLATE | INSERT SIZE, bp | SPECIFICITY | SENSITIVITY MOLECULES |
|---|---|---|---|
| MDV[1], ss[2] | | | 1000 |
| MDV[1]-SA1, ss[2] | 48 | Salmonella | 1500 |
| MDV[1]-SA2, ds[3] | 48 | Salmonella | 160 |
| MDV[1]-CA, ss[2] | 60 | Campylobacter | 2000 |
| MDV[1]-CA83, ss[2] | 83 | Campylobacter | 1500 |
| MDV[1]-CA29, ss[2] | 29 | Campylobacter | 2000 |
| MDV[1]-SH, ss[2] | 60 | Shigella | 500 |

[1]The template was isolated by purification of the Pst 1/Sma I fragment of the corresponding midivariant plasmid.
[2]The restriction fragment were denatured by base treatment.
[3]This template was not base treated.

TABLE IV

REPLICATION OF MIDIVARIANT FRAGMENTS

| TEMPLATE | CTP INCORPORATION, pmoles |
|---|---|
| MB2, 1 pmol | 0 |
| MB1SA1, 8 fmol | 0 |
| MASA5, 10 fmol | 0 |
| MB1SA1-MB2, 600 amol | 0 |

TABLE IV-continued
REPLICATION OF MIDIVARIANT FRAGMENTS

| TEMPLATE | CTP INCORPORATION, pmoles |
|---|---|
| MDSA1, 1 pmol | 0 |
| MC2SA5, 1 pmol | 0 |

TABLE V
INCORPORATION OF CTP INTO REPLICATION PRODUCTS

| Sample[1] | CTP Incorporated[2], pmoles |
|---|---|
| Ligated Template | 180 |
| Minus PM2058 Control | 0 |
| Minus Ligase Control | 0 |

[1] The template (1 fmol) amount for the ligated template sample is the total amount of template in the replication reaction assuming that the hybridization and legation steps were 100% efficient.
[2] The amount of CTP incorporated is for a 5 ul aliquot of the replication reaction out of a total volume of 50 ul.

We claim:

1. An amplification method for detecting the presence or absence of a target nucleic acid sequence in a test sample comprising:
   a) hybridizing at least two conjugates comprising midivariant DNA conjugated to a probe, each conjugate comprising:
      a nonreplicable oligomer of midivariant DNA; and
      a target-specific nucleic acid sequence complementary to a target sequence in the test sample;
   b) ligating the conjugates to form a replicable DNA template;
   c) replicating the template wherein the replication is catalyzed by Q Beta replicase; and
   d) detecting the replicated template which indicates the presence of the target nucleic acid sequence.

2. An amplification method as recited in claim 1 wherein at least one conjugate includes a promoter sequence attached to the conjugated midivariant DNA oligomer.

3. An amplification method as recited in claim 2 wherein said method further comprises the transcription of the midivariant DNA template to RNA by an RNA polymerase prior to replication.

4. An amplification method as recited in claim 1 wherein the hybridization of said at least two conjugates to the target nucleic acid sequence effects the contiguous alignment of the probes.

5. An amplification method as recited in claim 4 wherein the probes are ligated by T4 DNA ligase.

6. An amplification method as recited in claim 1 wherein at least one conjugate is immobilized on a solid support.

7. An amplification method as recited in claim 6 wherein the conjugate is released from the solid support before or after ligation of the probes.

8. An amplification method as recited in claim 6 wherein said solid support includes a paramagnetic particle.

9. An amplification method as recited in claim 8 wherein following hybridization, the hybridized conjugates are separated from the unhybridized conjugates and other components of the test sample by magnetic separation.

10. An amplification method as recited in claim 3 wherein said promoter sequence is a T7 RNA polymerase promotes sequence and the RNA polymerase is a T7 RNA polymerase.

11. An amplification method as recited in claim 1, wherein the nonreplicable midivariant DNA oligomer of one conjugate comprises the first 61 nucleotides of the 5' end of Q Beta midivariant (+) DNA, SEQ. NO.:1 and wherein the nonreplicable midivariant DNA oligomer of another conjugate comprises the remaining 3' nucleotides of Q Beta midivariant (+) DNA, SEQ. NO.: 2.

12. An amplification method as recited in claim 1 wherein at least one conjugate further comprises a nonspecific base sequence at its 5' terminus, the nonspecific base sequence including at least two nucleotide.

13. An amplification method as recited in claim 12 wherein at least one nucleotide of said nonspecific base sequence includes a a reactive group comprising a primary amine.

14. A method of detecting the presence or absence of a target nucleic acid sequence in a test sample comprising:
   a) contacting the target nucleic acid sequence with two conjugates comprising midivariant DNA conjugated to a probe under hybridizing conditions, each conjugate comprising: a nucleic acid sequence complementary to said target nucleic acid sequence and a nonreplicable midivariant DNA oligomer; wherein upon hybridization of the conjugates to the target nucleic acid sequence, the probes are contiguously aligned;
   b) ligating the conjugates, whereby a DNA template is formed;
   c) transcribing the DNA to form an RNA transcript;
   d) replicating the RNA transcript wherein the replication is catalyzed by Q Beta replicase; and
   e) detecting the replication product of step d) thereby detecting the presence of the target nucleic acid sequence.

15. An amplification method as recited in claim 1, wherein the nonreplicable midivariant DNA oligomer of one conjugate comprises the first 61 nucleotides of the 3' end of Q Beta midivariant (−) DNA, SEQ. NO.:3 and wherein the nonreplicable midivariant DNA oligomer of another conjugate comprises the remaining 5' nucleotides of Q Beta (−) midivariant DNA, SEQ. NO.:4.

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
    ( A ) LENGTH: 61 bases (B) TYPE: Nucleic Acid
(C) STRANDEDNESS: Single
(D) TOPOLOGY: Linear (ii) MOLECULE TYPE: Other Nucleic Acid
(A) DESCRIPTION: Bases 1-61 of the plus
strand of the midivariant nucleic acid
sequence from the 5'end.

(xi) SEQUENCE DESCRIPTION: SEQ ID NO:1:

| GGGGACCCCC | CGGAAGGGGG | GACGAGGTGC | GGGCACCTCG | 40 |
| TACGGGAGTT | CGACCGTGAC | A | | 61 |

(2) INFORMATION FOR SEQ ID NO:2:

(i) SEQUENCE CHARACTERISTICS:
(A) LENGTH: 160 bases
(B) TYPE: Nucleic Acid
(C) STRANDEDNESS: Single
(D) TOPOLOGY: Linear (ii) MOLECULE TYPE: Other Nucleic Acid
(A) DESCRIPTION: Bases 62-221 of the plus
strand of the midivariant nucleic acid
sequence from the 5'end.

(xi) SEQUENCE DESCRIPTION: SEQ ID NO:2:

| AGTCACGGGC | TAGCGCTTTC | GCGCTCTCCC | AGGTGACGCC | 40 |
| TCGTGAAGAG | GCGCGACCTT | CGTGCGTTTC | GGCGACGCAC | 80 |
| GAGAACCGCC | ACGCTGCTTC | GCAGCGTGGC | CCCTTCGCGC | 120 |
| AGCCCGCTGC | GCGAGGTGAC | CCCCGAAGG | GGGGTTCCCC | 160 |

(2) INFORMATION FOR SEQ ID NO:3:

(i) SEQUENCE CHARACTERISTICS:
(A) LENGTH: 61 bases
(B) TYPE: Nucleic Acid
(C) STRANDEDNESS: Single
(D) TOPOLOGY: Linear (ii) MOLECULE TYPE: Other Nucleic Acid
(A) DESCRIPTION: Bases 161-221 of the
minus strand of midivariant nucleic acid
sequence from the 3'end.

(xi) SEQUENCE DESCRIPTION: SEQ ID NO:3:

| TGTCACGGTC | GAACTCCCGT | ACGAGGTGCC | CGCACCTCGT | 40 |
| CCCCCTTCC | GGGGGGTCCC | C | | 61 |

(2) INFORMATION FOR SEQ ID NO:4:

(i) SEQUENCE CHARACTERISTICS:
(A) LENGTH: 160 bases
(B) TYPE: Nucleic Acid
(C) STRANDEDNESS: Single
(D) TOPOLOGY: Linear (ii) MOLECULE TYPE: Other Nucleic Acid
DESCRIPTION: Bases 1-160 of the minus strand of
the midivariant nucleic acid sequence from the 3'
end.

(xi) SEQUENCE DESCRIPTION: SEQ ID NO:4:

| GGGGAACCCC | CCTTCGGGGG | GTCACCTCGC | GCAGCGGGCT | 40 |
| GCGCGAAGGG | GCCACGCTGC | GAAGCAGCGT | GGCGGTTCTC | 80 |
| GTGCGTCGCC | GAAACGCACG | AAGGTCGCGC | CTCTTCACGA | 120 |
| GGCGTCACCT | GGGAGAGCGC | GAAAGCGCTA | GCCCGTGACT | 160 |

16. An amplification method for detecting the presence or absence of a target nucleic acid sequence in a test sample comprising: hybridizing at least two midivariant probe conjugates to a target nucleic acid sequence, each conjugate including: a midivariant sequence and a target specific nucleic acid sequence which is complementary to the target nucleic acid sequence; ligating the conjugates to form a midivariant template; replicating the template, wherein the replication is catalyzed by Q Beta replicase and detecting the replication product to detect the presence of the target nucleic acid sequence.

* * * * *